(12) United States Patent
Ding et al.

(10) Patent No.: US 10,654,856 B2
(45) Date of Patent: May 19, 2020

(54) METHOD FOR PREPARING PYRROLO[3,2-D]PYRIMIDINE COMPOUND, AND INTERMEDIATES THEREOF

(71) Applicant: CHIA TAI TIANQING PHARMACEUTICAL GROUP CO., LTD., Jiangsu, Lianyungang (CN)

(72) Inventors: Zhaozhong Ding, Shanghai (CN); Fei Sun, Shanghai (CN); Yinghu Hu, Shanghai (CN); Yilong Zhou, Shanghai (CN); Rui Zhao, Lianyungang (CN); Ling Yang, Lianyungang (CN)

(73) Assignee: CHIA TAI TIANQING PHARMACEUTICAL GROUP CO., LTD., Jiangsu, Lianyungang (CN)

( * ) Notice: Subject to any disclaimer, the term of this patent is extended or adjusted under 35 U.S.C. 154(b) by 0 days.

(21) Appl. No.: 16/075,300

(22) PCT Filed: Feb. 4, 2017

(86) PCT No.: PCT/CN2017/072893
§ 371 (c)(1),
(2) Date: Aug. 3, 2018

(87) PCT Pub. No.: WO2017/133686
PCT Pub. Date: Aug. 10, 2017

(65) Prior Publication Data
US 2019/0040072 A1     Feb. 7, 2019

(30) Foreign Application Priority Data
Feb. 5, 2016  (CN) .......................... 2016 1 0082028

(51) Int. Cl.
*C07D 487/04* (2006.01)

(52) U.S. Cl.
CPC .................. *C07D 487/04* (2013.01)

(58) Field of Classification Search
CPC .................................................. C07D 487/04
See application file for complete search history.

(56) References Cited

U.S. PATENT DOCUMENTS

| | | |
|---|---|---|
| 2010/0143301 A1 | 6/2010 | Desai et al. |
| 2017/0273983 A1 | 9/2017 | Ding et al. |
| 2019/0040071 A1* | 2/2019 | Ding .................. A61P 31/12 |

FOREIGN PATENT DOCUMENTS

| | | |
|---|---|---|
| CN | 105367576 A | 3/2016 |
| EP | 3 190 113 A1 | 7/2017 |
| EP | 3 381 918 A1 | 10/2018 |
| WO | WO-2009/082247 A1 | 7/2009 |
| WO | WO-2014/081644 A1 | 5/2014 |
| WO | WO-2014/081645 A1 | 5/2014 |
| WO | WO-2016/023511 A1 | 2/2016 |
| WO | WO-2017/076346 A1 | 5/2017 |
| WO | WO-2017/133684 A1 | 8/2017 |

OTHER PUBLICATIONS

International Search Report and Written Opinion, dated May 11, 2017, issued in corresponding International Application No. PCT/CN2017/072893.
Mahadevan, et al., "A General Method for C3 Reductive Alkylation of Indoles", Tetrahedron Letters 44: 4589-4591 (2003).
European Extended Search Report, issued in European Patent Appln. No. 17747006.9, 6 pages (dated Jun. 3, 2019).
Israeli Office Action, issued in Israeli Patent Appln. No. 260999, 3 pages (dated Mar. 26, 2019).
Lanford, et al., "GS-9620, and Oral Agonist of Toll-Like Receptor-7, Induces Prolonged Suppression of Hepatitis B Virus in Chronically Infected Chimpanzees", Gastroenterology 144: 1508-1517 (2013).
Sauder, et al., "Imiquimod: modes of action", British Journal of Dermatology 149 (Suppl. 66): 5-8 (2003).
Wu, et al., "Resiquimod: a new immune response modifier with potential as a vaccine adjuvant for Th1 immune responses", Antiviral Research 64: 79-83 (2004).
Chinese Office Action, issued in Chinese Pat. App. No. 201780009748.X, 26 pages (dated Sep. 30, 2019).
Singaporean Written Opinion, issued in Singaporean Pat. App. No. 11201806685V, 6 pages (dated Sep. 26, 2019).
Chilean Office Action, issued in Chilean Pat. App. No. 201802094, 12 pages (dated Jul. 17, 2019).

* cited by examiner

*Primary Examiner* — Brian E McDowell
(74) *Attorney, Agent, or Firm* — Foley & Lardner LLP

(57) ABSTRACT

The present invention relates to a method for preparing a pyrrolo[3,2-d]pyrimidine compound (the compound represented by formula I), and corresponding intermediates.

(I)

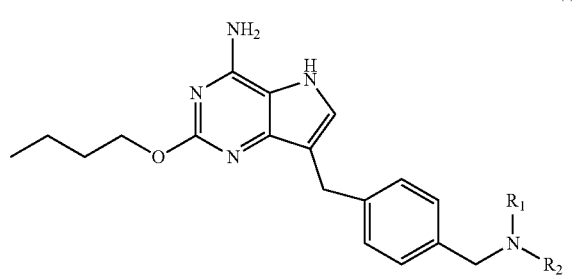

17 Claims, No Drawings

METHOD FOR PREPARING PYRROLO[3,2-D]PYRIMIDINE COMPOUND, AND INTERMEDIATES THEREOF

CROSS-REFERENCE TO RELATED APPLICATIONS

This application is a national phase of International Application No. PCT/CN2017/072893, filed on Feb. 4, 2017, which claims priority to Chinese Patent Application No. 201610082028.3, filed on Feb. 5, 2016, each of which is incorporated herein by reference in its entirety.

TECHNICAL FIELD

The present invention relates to the field of medicinal chemistry and specifically relates to a process for preparing pyrrolo[3,2-d]pyrimidine compound and the intermediate thereof.

BACKGROUND

Toll-like receptor is expressed by various immune cells and recognizes high reserved structural motifs: Pathogen Associated Molecular Pattern (PAMP) expressed by microorganism pathogens or Damage Associated Molecular Patterns (DAMP) released by dead cells. PAMP or DAMP stimulates Toll-like receptor to trigger signal cascade which induces the activations of transcriptional factors like AP-1, NF-κB and interferon regulators (pulse response function). It results in various cell responses, including productions of interferons, proinflammatory cytokines and effector cytokines, whereby immune response is produced. By far, 13 types of Toll-like receptors have been discovered in mammal. Toll-like receptors 1, 2, 4, 5 and 6 are mainly expressed on the cell surface while Toll-like receptors 3, 7, 8 and 9 are expressed in the endosome. Different Toll-like receptors recognize ligands derived from different pathogens. Toll-like receptor 7 (TLR7) is mainly expressed by plasmaeytoid dendritic cells (pDC), and recognized via ligand to induce the secretion of interferon α (IFN-α). Toll-like receptor 7 (TLR7) and Toll-like receptor 8 (TLR8) are highly homologous and therefore the ligand of TLR7 in most cases is also that of TLR8. TLR8 stimulation mainly induces the productions of cytokines like tumor necrosis factor α (TNF-α) and chemoattractant. Interferon α is one of the medicines for treating chronic hepatitis B or hepatitis C while TNF-α is a proinflammatory cytokine, of which the over secretion will result severe side effects. There have been reported several TLR7 agonists, like imiquimod (British Journal of Dermatology 2003; 149 (Suppl. 66): 5-8), resiquimod (Antiviral Research 64 (2004) 79-83), GS-9620(Gastroenterology (2013), 144(7), 1508-1517). Nevertheless, it is desirable to have novel TLR7 agonists with better selectivity, activity and safety.

Chinese Patent Application No. 201410405136.0 which is incorporated in its entirety by reference herein discloses a series of pyrrolopyrimidine compounds as TLR7 agonist.

SUMMARY

In an aspect, provided is a process for preparing the compound of formula I:

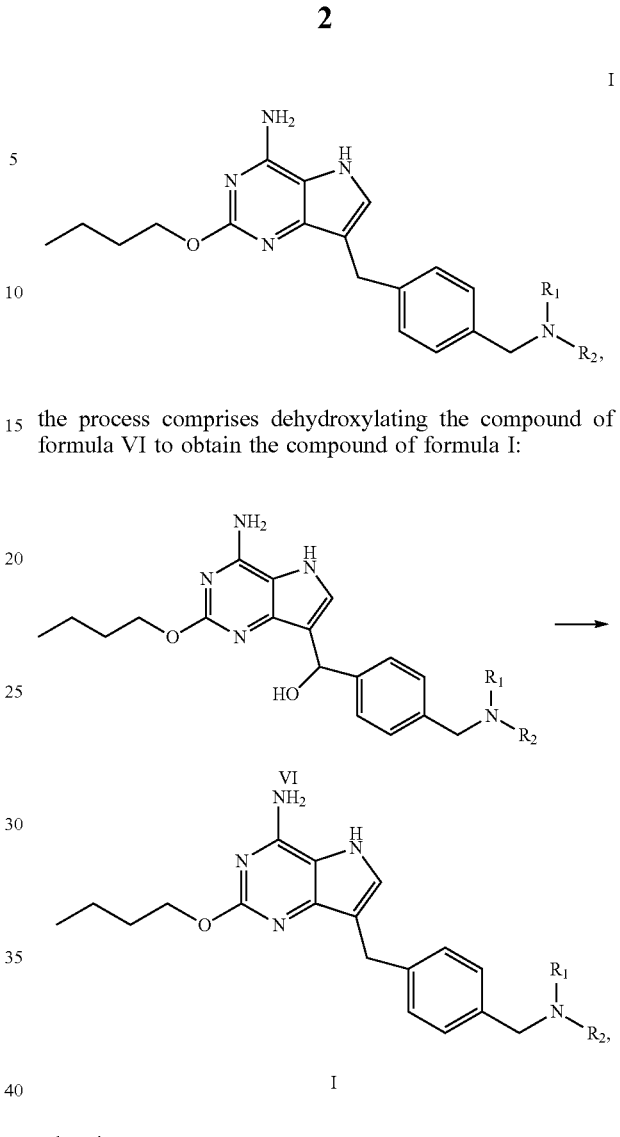

the process comprises dehydroxylating the compound of formula VI to obtain the compound of formula I:

wherein $R_1$ and $R_2$ are independently selected from the group consisting of $C_{1-4}$ alkyl, or $R_1$ and $R_2$ together with the N atom attached thereto form 4~8 membered heterocycloalkyl, wherein the heterocycloalkyl is optionally substituted with one or more substituents independently selected from the group consisting of hydroxyl, halogen, $C_{1-4}$ alkyl and $C_{1-4}$ alkoxy.

DETAILED DESCRIPTION

Definition

Unless stated otherwise, the terms and phrases used herein have the following meaning. A specific term or phrase shall not be considered as unclear or indefinite when it is not specifically defined. It should be understood according to the general meaning. The trade name used herein refers to the corresponding product or the active ingredient.

Unless specifically defined otherwise, proportion (including percentage) or part is calculated based on weight herein.

When used with a numerical variable, the term "approximate" or "about" usually refers to the value of the variable and all the values of the variable within the experimental error (for example, within an average 95% confidence interval) or within ±10% of the specified value, or a wider range.

The expression "comprise" or its synonyms "contain", "include", "have" or the like is open-ended, which does not exclude other unlisted elements, steps or ingredients. The expression "consist of" excludes any unlisted elements, steps or ingredients. The expression "substantially consist of" refers to specified elements, steps or ingredients within a given range, together with optional elements, steps or components which do not substantively affect the basic and novel feature of the claimed subject matter. It should be understood that the expression "comprise" encompasses the expressions "substantially consist of" and "consist of".

The term "optional" or "optionally" means the event described subsequent thereto may or may not happen. This term encompasses the cases that the event may or may not happen.

The expression $C_{m-n}$ used herein means that it has m-n carbon atoms. For example, "$C_{1-4}$ alkyl" means said alkyl has 1-4 carbon atoms.

The numerical range herein refers to each of the integers therein and the subranges formed by the integers. For example, "$C_{1-4}$" means said group may have 1 carbon atom, 2 carbon atoms, 3 carbon atoms or 4 carbon atoms. Accordingly, "$C_{1-4}$ alkyl" encompasses "$C_{2-3}$ alkyl", "$C_{1-3}$ alkyl", "$C_{2-4}$ alkyl", as well as $C_1$ alkyl, $C_2$ alkyl, $C_3$ alkyl, $C_4$ alkyl or the like.

The term "substituted" means that one or more hydrogen atoms on a given atom are replaced by a substituent, provided that the valence of the particular atom is normal and the compound after substitution is stable.

Unless stated otherwise, the term "hetero" means heteroatom or hetero-radical (i.e. a radical containing heteroatom), i.e. the atoms beyond carbon and hydrogen atoms or the radical containing such atoms. Preferably, the heteroatom is independently selected from the group consisting O, N, S etc. In an embodiment wherein two or more heteroatoms are involved, the two or more heteroatoms may be the same or part or all of the two or more heteroatoms may be different.

The term "alkyl" refers to a linear or branched saturated aliphatic hydrocarbyl group consisting of carbon and hydrogen atoms, which is linked to rest of the molecule via a single bond. Non-limiting examples of $C_{1-4}$ alkyl comprise but not limited to methyl, ethyl, propyl, isopropyl, n-butyl, isobutyl, sec-butyl, tert-butyl or the like.

The term "$C_{1-4}$ alkoxy" refers to "$C_{1-4}$ alkyl" which is connected to the rest of the molecule via "—O—", wherein the "$C_{1-4}$ alkyl" is defined as above.

The term "halo" or "halogen" refers to F, Cl, Br or I.

The term "hydroxyl" refers to —OH group.

The N atom in the expression "$R_1$ and $R_2$ together with the N atom attached thereto" refers to the N atom in the moiety

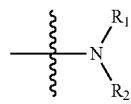

in the formula.

The term "heterocycloalkyl" refers to a saturated monocyclic or polycyclic system group, wherein part of the ring atoms are heteroatoms selected from the group consisting of N, O, S, and rest of the ring atoms are C. Accordingly, the term "4~8 membered heterocycloalkyl" refers to the heterocycloalkyl containing 4-8 ring atoms in the system, wherein one or more ring atoms are heteroatoms selected from the group consisting of N, O, S. "4~8 membered heterocycloalkyl" encompasses "4~7 membered", "4~6 membered", "5~7 membered" heterocycloalkyl, for example but not limited to 4, 5, 6, 7, 8 membered heterocycloalkyl. The examples of 4 membered heterocycloalkyl comprise but not limited to azetidinyl; the examples of 5 membered heterocycloalkyl comprise but not limited to pyrrolidinyl, isoxazolidinyl, oxazolidinyl, isothiazolidinyl, thiazolidinyl, imidazolidinyl; the examples of 6 membered heterocycloalkyl comprise but not limited to piperidinyl, morpholinyl, piperazinyl; and the examples of 7 membered heterocycloalkyl comprise but not limited to azacycloheptanyl, oxaazabicyclo[2.2.1]heptyl, or the like.

The term "one or more" refers to one, two, three, four, five, six, seven, eight or more.

The following abbreviations are used herein: SEM: 2-(trimethylsilyl)ethoxymethyl; SEM-Cl: 2-(trimethylsilyl)ethoxymethyl chloride; DIPEA: diisopropyl ethyl amine; TFA: trifluoroacetic acid; DMF: N,N-dimethylformamide; n-BuOH: n-butanol.

Process for Preparing the Compound of Formula I

In an aspect, provided is a process for preparing the compound of formula I, the process comprises dehydroxylating the compound of formula VI to obtain the compound of formula I:

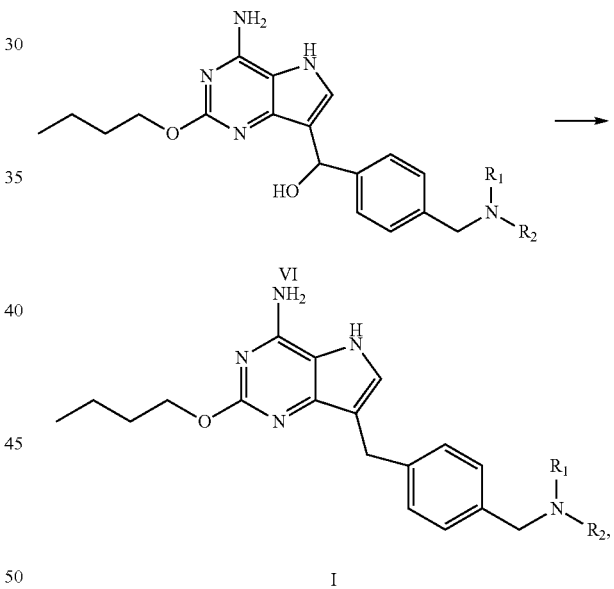

wherein $R_1$ and $R_2$ are independently selected from the group consisting of $C_{1-4}$ alkyl, or $R_1$ and $R_2$ together with the N atom attached thereto form 4~8 membered heterocycloalkyl, wherein the heterocycloalkyl is optionally substituted with one or more substituents independently selected from the group consisting of hydroxyl, halogen, $C_{1-4}$ alkyl and $C_{1-4}$ alkoxy.

In an embodiment, the process for preparing the compound of formula I according to the invention comprises the following steps:

(a) reacting the compound of formula II with the compound of formula III in the presence of base to obtain the compound of formula IV

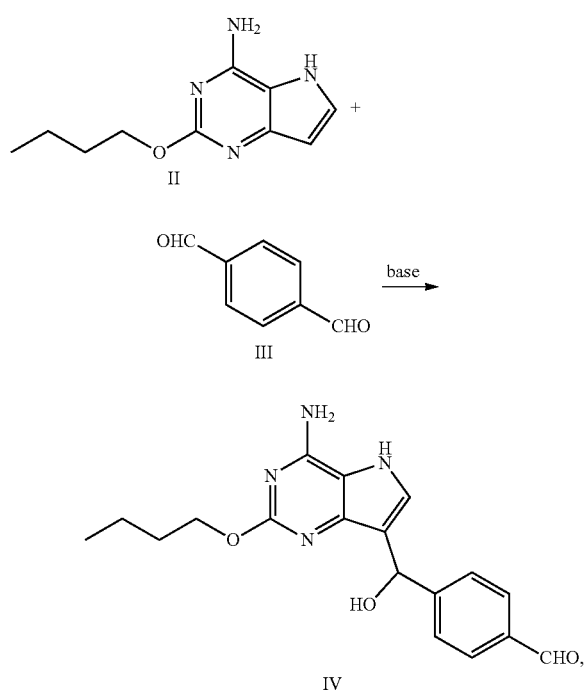

(b) reacting the compound of formula IV with the compound of formula V in the presence of reductant to obtain the compound of formula VI

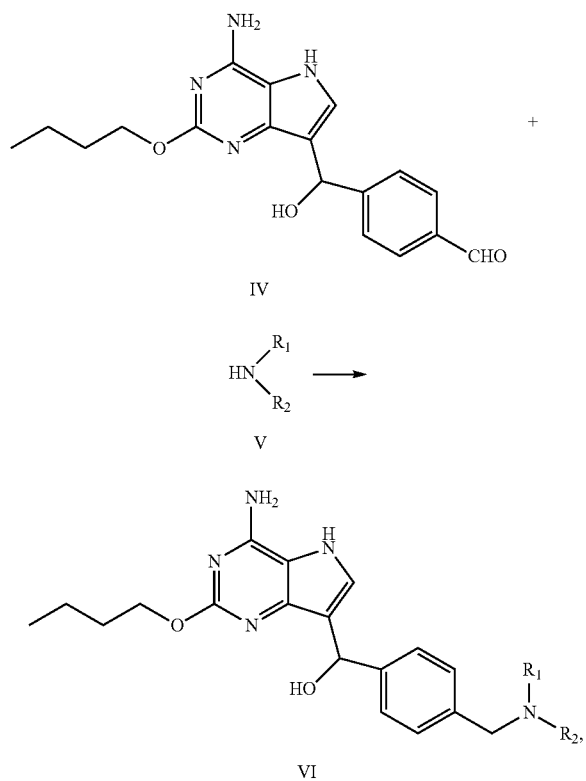

(c) dehydroxylating the compound of formula VI to obtain the compound of formula I

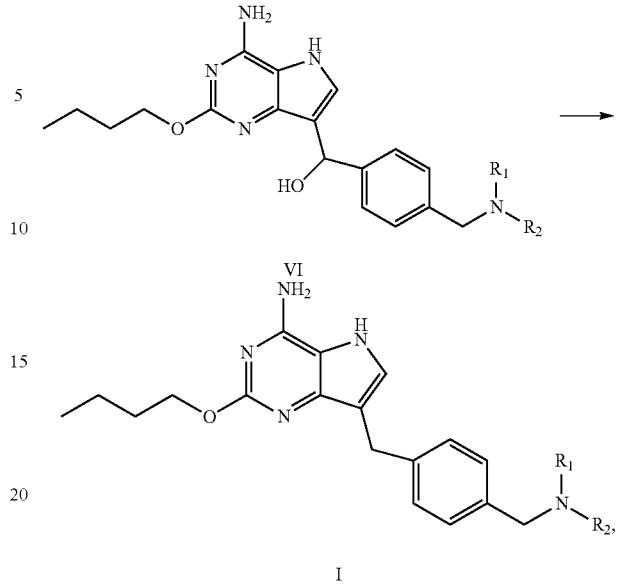

wherein $R_1$ and $R_2$ are independently selected from the group consisting of $C_{1-4}$ alkyl, or $R_1$ and $R_2$ together with the N atom attached thereto form 4~8 membered heterocycloalkyl, wherein the heterocycloalkyl is optionally substituted with one or more substituents independently selected from the group consisting of hydroxyl, halogen, $C_{1-4}$ alkyl and $C_{1-4}$ alkoxy.

In an embodiment, the base is selected from the group consisting of sodium carbonate, sodium bicarbonate, potassium carbonate, potassium phosphate, potassium bicarbonate, cesium carbonate, lithium hydroxide, sodium hydroxide, potassium hydroxide, calcium hydroxide, magnesium hydroxide, barium hydroxide, sodium methoxide, sodium ethoxide, sodium t-butoxide, potassium t-butoxide, triethylamine, diisopropylethylamine, pyridine, N,N-dimethylaminopyridine, piperidine, N-methylpiperidine, morpholine, N-methylmorpholine and any combination thereof, preferably sodium carbonate, potassium carbonate, sodium hydroxide, potassium hydroxide and any combination thereof, most preferably potassium carbonate.

In an embodiment, step (a) is performed in a solvent. In a preferred embodiment, the solvent is isopropanol or a mixture of isopropanol with water.

In an embodiment, the molar ratio of the compound of formula II to the base is 1.0:1.0~3.0, preferably 1.0:1.0~1.5, more preferably 1.0:1.2.

In an embodiment, the molar ratio of the compound of formula II to the compound of formula III is 1.0:1.0~3.0, preferably 1.0:1.0~1.5, more preferably 1.0:1.2~1.5.

In an embodiment, the step (b) is performed in the presence of acid. In another embodiment, the acid is selected from the group consisting of hydrochloric acid, hydrobromic acid, phosphoric acid, sulfuric acid, formic acid, acetic acid, propionic acid, citric acid, fumaric acid, malic acid, succinic acid, salicylic acid, maleic acid, trifluoroacetic acid and any combination thereof, preferably acetic acid.

In an embodiment, in step (b), the molar ratio of the compound of formula IV to the acid is 1.0:1.0~3.0, preferably 1.0:1.2~2.0, more preferably 1.0:1.5.

In an embodiment, the step (b) is conducted in a solvent. In a preferred embodiment, the solvent is isopropanol or a mixture of isopropanol with water.

In an embodiment, the reductant is selected from the group consisting of BH$_3$, NaBH$_4$, NaBH$_3$CN, NaBH(AcO)$_3$ and any combination thereof, preferably NaBH(AcO)$_3$.

In an embodiment, the molar ratio of the compound of formula IV to the reductant is 1.0:1.0~3.0, preferably 1.0:1.2~2.0, more preferably 1.0:1.5.

In a preferred embodiment, the dehydroxylation is performed in the presence of triethylsilane and trifluoroacetic acid.

In another preferred embodiment, the molar ratio of the compound of formula VI to triethylsilane is 1:1~10, preferably 1:2~8, more preferably 1:5.

In another preferred embodiment, the molar ratio of the compound of formula VI to trifluoroacetic acid is 1:2~20, preferably 1:5~15, more preferably 1:10~12.

In an embodiment, the step (c) is performed in a solvent. In a preferred embodiment, the solvent is dichloromethane.

In another embodiment, the process for preparing the compound of formula I according to the invention comprises the following steps:

(a') reacting the compound of formula II with the compound of formula III' in the presence of base to obtain the compound of formula VI

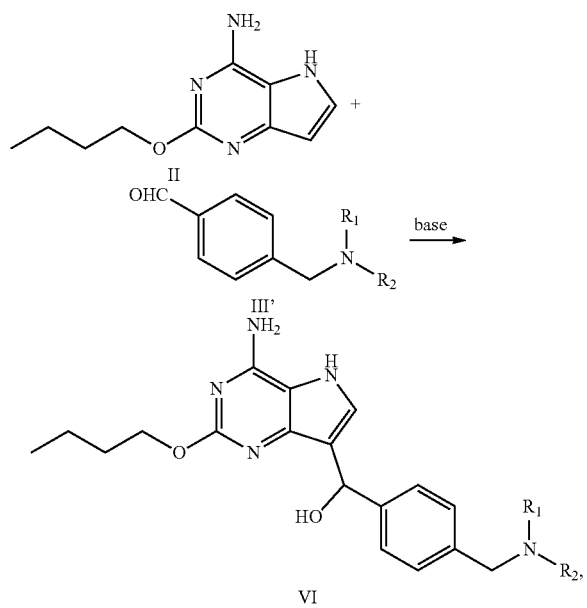

(b') dehydroxylating the compound of formula VI to obtain the compound of formula I

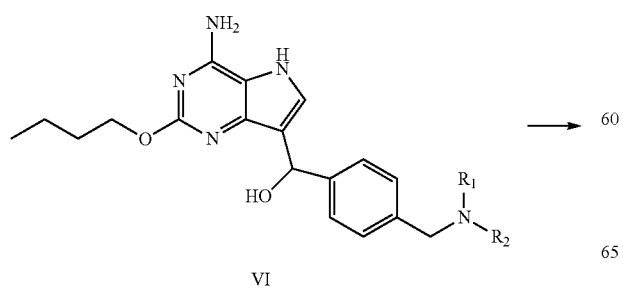

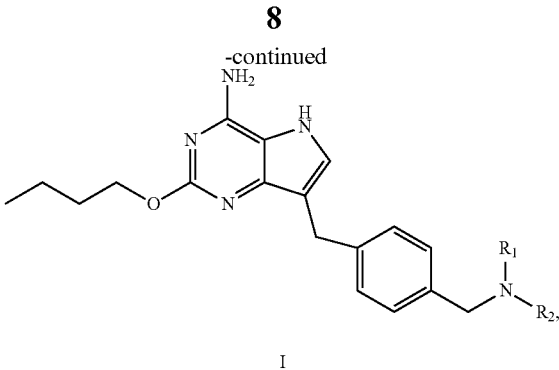

wherein

R$_1$ and R$_2$ are independently selected from the group consisting of C$_{1-4}$ alkyl, or R$_1$ and R$_2$ together with the N atom attached thereto form 4~8 membered heterocycloalkyl, wherein the heterocycloalkyl is optionally substituted with one or more substituents independently selected from the group consisting of hydroxyl, halogen, C$_{1-4}$ alkyl and C$_{1-4}$ alkoxy.

In an embodiment, the base is selected from the group consisting of sodium carbonate, sodium bicarbonate, potassium carbonate, potassium phosphate, potassium bicarbonate, cesium carbonate, lithium hydroxide, sodium hydroxide, potassium hydroxide, calcium hydroxide, magnesium hydroxide, barium hydroxide, sodium methoxide, sodium ethoxide, sodium t-butoxide, potassium t-butoxide, triethylamine, diisopropylethylamine, pyridine, N,N-dimethylaminopyridine, piperidine, N-methylpiperidine, morpholine, N-methylmorpholine and any combination thereof, preferably sodium carbonate, potassium carbonate, sodium hydroxide, potassium hydroxide and any combination thereof, most preferably potassium carbonate.

In an embodiment, the step (a') is performed in a solvent. In a preferred embodiment, the solvent is methanol or a mixture of methanol with water.

In an embodiment, the molar ratio of the compound of formula II to the base is 1.0:1.0~3.0, preferably 1.0:1.0~1.5, more preferably 1.0:1.2.

In an embodiment, the molar ratio of the compound of formula II to the compound of formula III' is 1.0:1.0~3.0, preferably 1.0:1.0~1.5, more preferably 1.0:1.2~1.5.

In a preferred embodiment, the dehydroxylation is performed in the presence of triethylsilane and trifluoroacetic acid.

In another preferred embodiment, the molar ratio of the compound of formula VI to triethylsilane is 1:1~10, preferably 1:2~8, more preferably 1:5.

In another preferred embodiment, the molar ratio of the compound of formula VI to trifluoroacetic acid is 1:2~20, preferably 1:5~15, more preferably 1:10~12.

In an embodiment, the step (b') is performed in a solvent. In a preferred embodiment, the solvent is dichloromethane.

In an embodiment, the compound of formula V is selected from

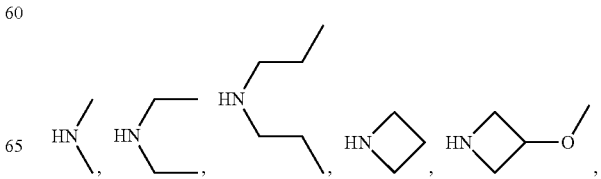

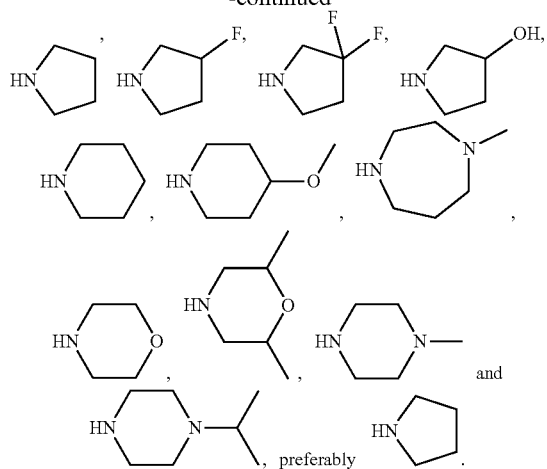
In a preferable embodiment, the compound of formula I is selected from the compounds numbered as follows:
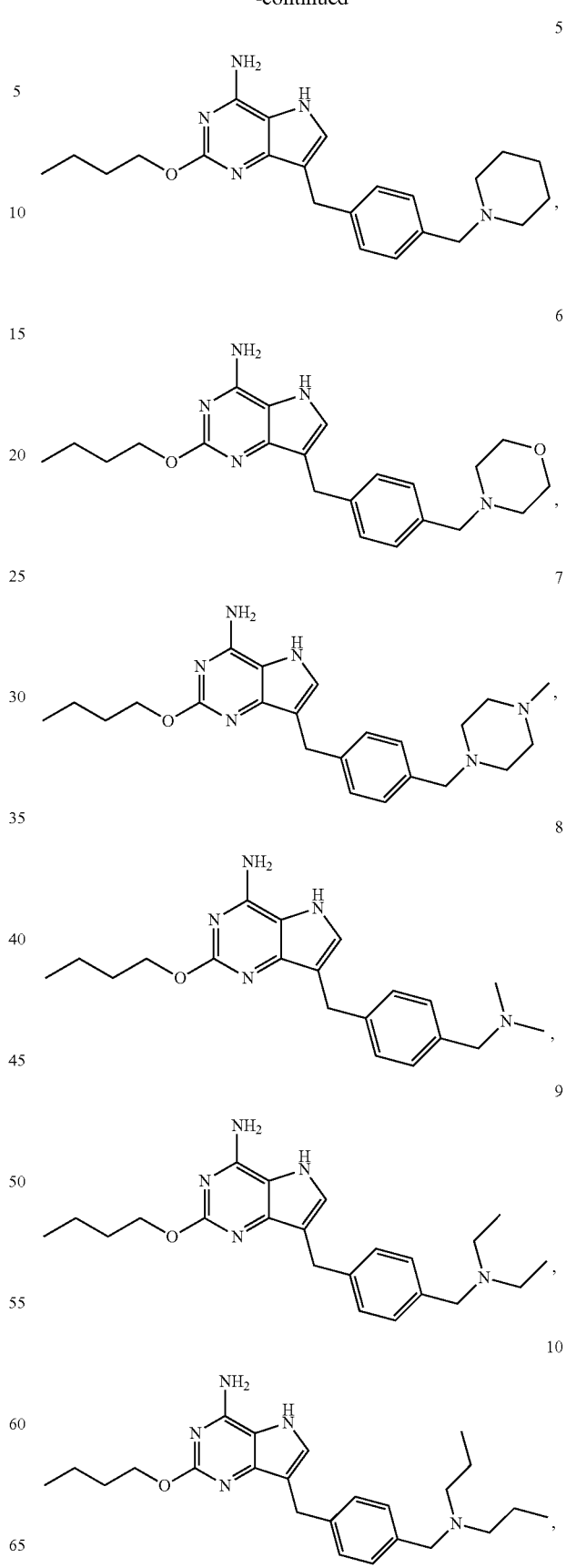

-continued

11

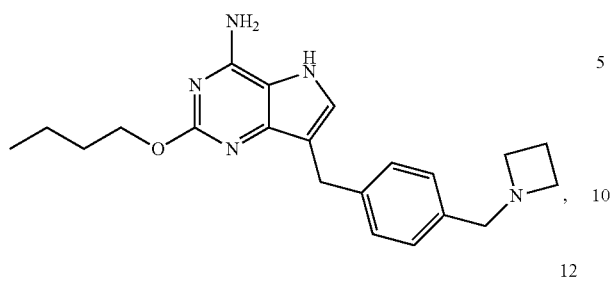

12

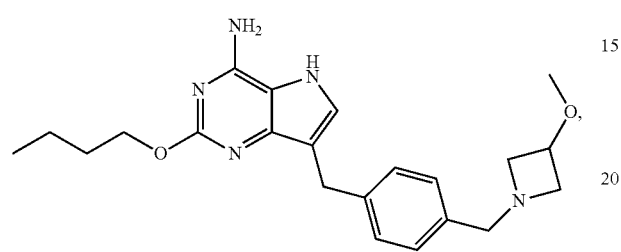

13

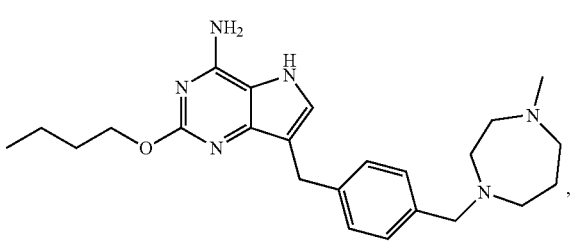

14

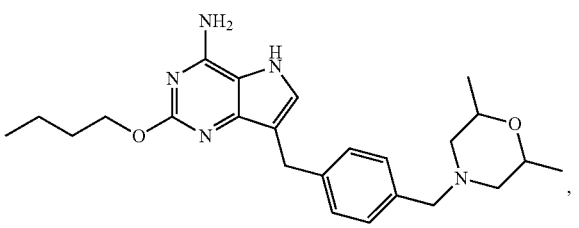

15

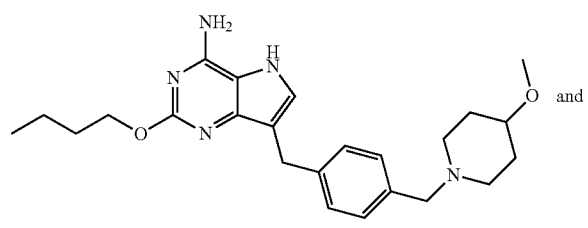 and

16

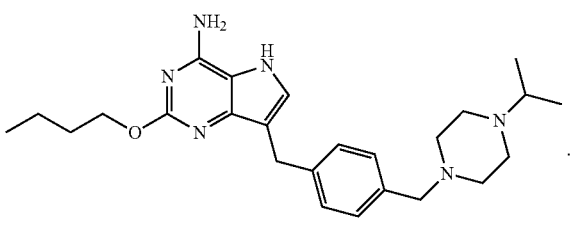

Intermediate Compound and Preparation

Provided are the compound of formula II and the compound of formula VI as intermediate:

II

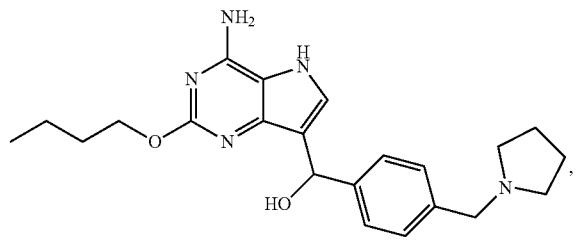,

VI

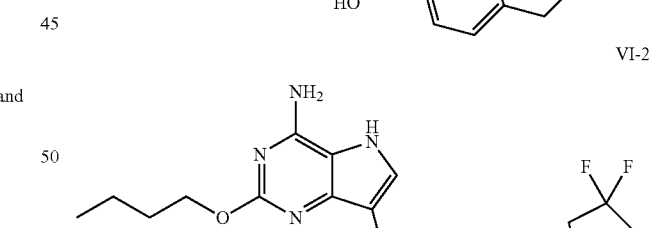

wherein

R₁ and R₂ are independently selected from the group consisting of $C_{1-4}$ alkyl, or R₁ and R₂ together with the N atom attached thereto form 4~8 membered heterocycloalkyl, wherein the heterocycloalkyl is optionally substituted with one or more substituents independently selected from the group consisting of hydroxyl, halogen, $C_{1-4}$ alkyl and $C_{1-4}$ alkoxy.

In an embodiment, the compound of formula VI is selected from

VI-1

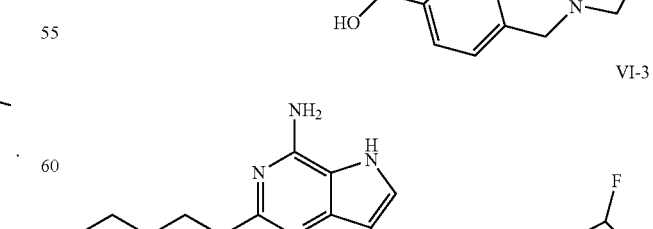,

VI-2

VI-3

-continued

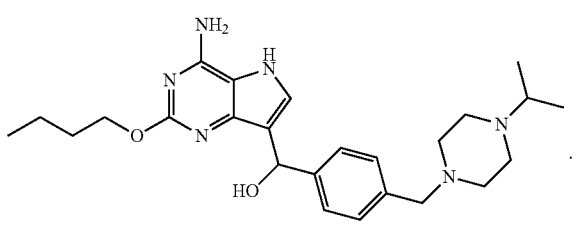

The compound of formula II according to the invention may be prepared through the following process.

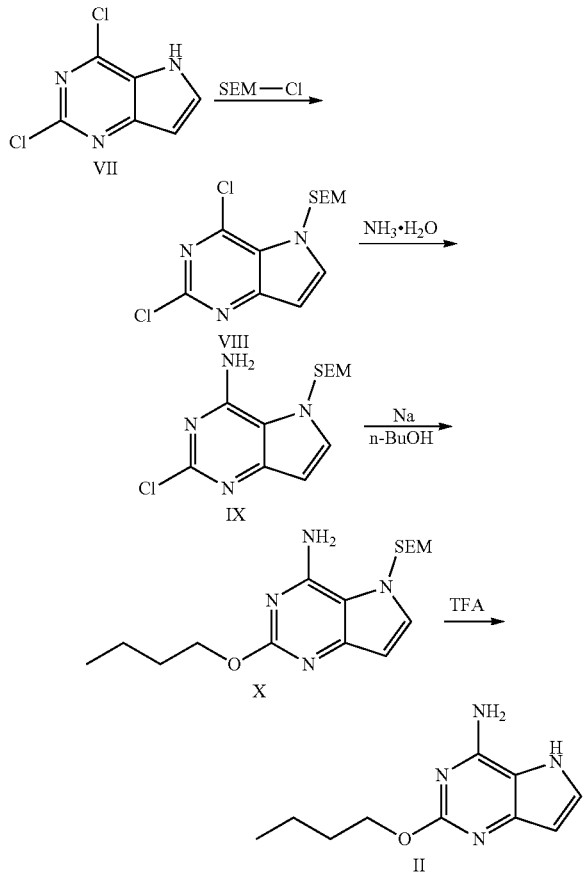

wherein, reacting the compound of formula VII with SEM-Cl to obtain the compound of formula VIII (preferably in DMF);

reacting the compound of formula VIII with aqueous ammonia to obtain the compound of formula IX (preferably in isopropanol);

subjecting the compound of formula IX to substitution reaction with sodium n-butoxide to form the compound of formula X (preferably in n-BuOH); and removing SEM from the compound of formula X under the action of TFA to obtain the compound of formula II (preferably in TFA).

Beneficial Effect

The preparing process according to the invention has mild reaction conditions, for example the reaction may be conducted under atmospheric pressure (e.g. about 1 atm), and the requirement for reaction temperature is normal. The preparing process according to the invention can also avoid the use of reagents with high cost and risks and is particularly suitable for industrial production.

EXAMPLES

To better understand the invention, further illustration will be given below with reference to the following examples. The specific examples, however, are not intended to limit the scope of the present invention.

Preparation Example 1

The preparation example of the compound of formula I:

Preparation of 2-butoxy-7-(4-(pyrrolidin-1-ylmethyl)benzyl)-5H-pyrrolo[3,2-d]pyrimidin-4-amine (the Compound of Formula I of No. 1)

Preparation of 4-((4-amino-2-butoxy-5H-pyrrolo[3,2-d]pyrimidin-7-yl)-hydroxylmethyl)benzaldehyde (the Compound of Formula IV)

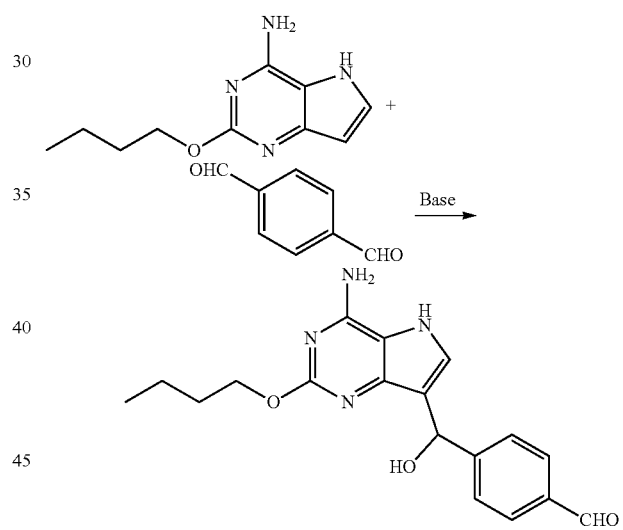

To a three-necked flask were added terephthalic aldehyde (790.64 mg, 5.82 mmol) and isopropanol (10 mL), followed by addition of 2-butoxy-5H-pyrrolo[3,2-d]pyrimidin-4-amine (1.00 g, 4.85 mmol) with stirring. Stirring was performed for 10 min after the system was cooled to 0° C. Purified water (10 mL) and potassium carbonate (804.17 mg, 5.82 mmol) were added, and the reaction was performed at 25° C. for 16 h until the raw materials were depleted with the monitor by LCMS. After completion of the reaction, solid was precipitated out. Filtration was performed and the solid was slurried with 20 ml of purified water and 30 ml (ethyl acetate/n-heptane=1/20) successively. Filtration was performed and drying was conducted to give the title compound as yellow solid (1.50 g, 4.41 mmol, yield: 90.9%).

$^1$H NMR (400 MHz, methanol-$d_4$) δ 9.94 (s, 1H), 7.86 (d, J=8.16 Hz, 2H), 7.72 (d, J=8.16 Hz, 2H), 7.12-7.17 (m, 1H), 6.19 (s, 1H), 4.28 (t, J=6.53 Hz, 2H), 1.68-1.77 (m, 2H), 1.44-1.54 (m, 2H), 0.97 (t, J=7.34 Hz, 3H).

Preparation of (4-amino-2-butoxy-5H-pyrrolo[3,2-d]pyrimidin-7-yl)(4-(pyrrolidin-1-ylmethyl)phenyl)methanol (the Compound of Formula VI-1)

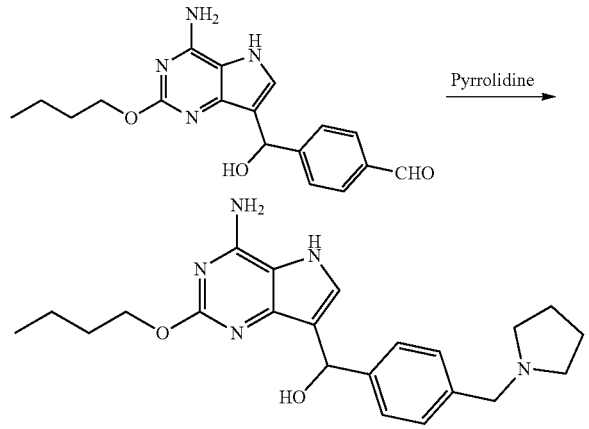

To 30 L clave were added the above obtained compound of formula IV 4-((4-amino-2-butoxy-5H-pyrrolo[3,2-d]pyrimidin-7-yl)-hydroxylmethyl)benzaldehyde (450.0 g, 1.32 mol) and isopropanol (4.5 L). After stirring for 5 min, glacial acetic acid (119.0 g, 1.98 mol) was added. The system was stirred until it was cooled to 0-10° C. Pyrrolidine (112.4 g, 1.58 mol) was added dropwise during which the temperature of the system was kept below 10° C. After addition, sodium triacetoxyborohydride (NaBH(AcO)$_3$) (420.0 g, 1.98 mol) was added in portions. The reaction was carried out at 10-20° C. for 3 h until the raw materials were depleted with the monitor by liquid chromatography. After the completion of reaction, 5 L of purified water was added and the temperature of the solution was lowered to about −10° C. 12 L of 15% aqueous ammonia was added during which the temperature of the solution was kept below 0° C. Solid was precipitated out under stirring. Filtration was performed and the solid was slurried with 2 L of water and 2 L×2 ethyl acetate successively. Filtration was performed and drying was conducted at 40° C. under reduced pressure for 12 h to give the title compound as yellow solid (465.0 g, 1.18 mol, yield 89.4%, moisture 0.9%).

$^1$H NMR (400 MHz, methanol-d$_4$) δ 7.46 (d, J=7.91 Hz, 1H), 7.29 (d, J=8.03 Hz, 1H), 7.09 (s, 1H), 6.12 (s, 1H), 4.29 (t, J=6.53 Hz, 2H), 3.60 (s, 2H), 2.52 (br. s., 4H), 1.66-1.83 (m, 6H), 1.49 (d, J=7.53 Hz, 2H), 0.98 (t, J=7.40 Hz, 3H).

The compound of formula VI-1 can also be prepared according to the following process:

Preparation of (4-amino-2-butoxy-5H-pyrrolo[3,2-d]pyrimidin-7-yl)(4-(pyrrolidin-1-ylmethyl)phenyl)methanol (the Compound of Formula VI-1)

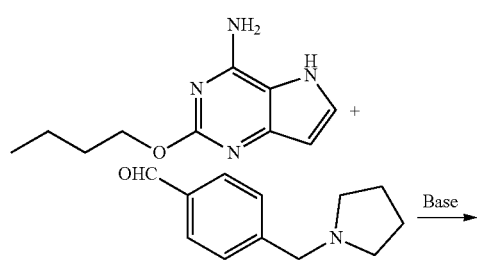

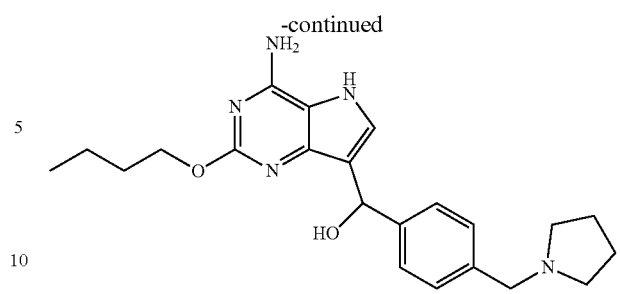

To the mixture of 2-butoxy-5H-pyrrolo[3,2-d]pyrimidin-4-amine (3.00 g, 14.55 mmol), 4-(pyrrolidin-1-ylmethyl)benzaldehyde (4.13 g, 21.82 mmol), methanol (30 mL) and water (30 mL) was added potassium carbonate (2.41 g, 17.46 mmol) with stirring. Then stirring was performed at 25° C. for 12 h and raw materials were depleted with the monitor by thin-layer chromatography. Solid was precipitated out after completion of the reaction. 30 mL of water was added, and the solid was filtered and dried to give the title compound as white solid (3.50 g, 8.85 mmol, yield: 60.82%).

$^1$H NMR (400 MHz, methanol-d$_4$) δ 7.46 (d, J=7.91 Hz, 1H), 7.29 (d, J=8.03 Hz, 1H), 7.09 (s, 1H), 6.12 (s, 1H), 4.29 (t, J=6.53 Hz, 2H), 3.60 (s, 2H), 2.52 (br. s., 4H), 1.66-1.83 (m, 6H), 1.49 (d, J=7.53 Hz, 2H), 0.98 (t, J=7.40 Hz, 3H).

Preparation of 2-butoxy-7-(4-(pyrrolidin-1-ylmethyl)benzyl)-5H-pyrrolo[3,2-d]pyrimidin-4-amine (the Compound of Formula I of No. 1)

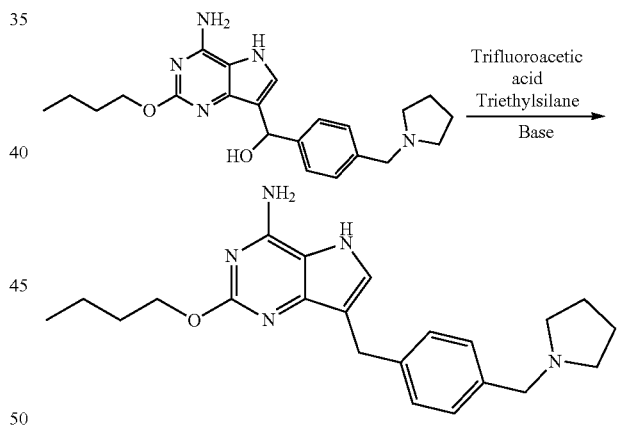

To 20 L clave were added the above obtained compound of formula VI-1 (4-amino-2-butoxy-5H-pyrrolo[3,2-d]pyrimidin-7-yl)(4-(pyrrolidin-1-ylmethyl)phenyl)methanol (440.0 g, 1.11 mol) and dichloromethane (7.0 L). The system was stirred until it was cooled to below −15° C. Triethylsilane (880 mL, 5.55 mol) was added dropwise followed by trifluoroacetic acid (880 mL, 11.84 mol) dropwise during which the temperature of the system was kept below −10° C. After addition, the reaction was carried out at 0° C. for 2 h until the raw material point disappeared with the monitor by liquid chromatography. After the completion of reaction, the reaction liquid was concentrated to dryness, 2.2 L of ethyl acetate was added and the system was cooled to below 0° C. with stirring. Saturated sodium carbonate solution was added to adjust pH to 9-10, during which the temperature was kept below 10° C. Filtration was performed and the obtained filter cake was slurried with 2.2 L of water. Drying was conducted under reduced pressure to give 550 g of 2-butoxy-7-(4-(pyrrolidin-1-ylmethyl)benzyl)-5H-pyrrolo[3,2-d]pyrimidin-4-amine (trifluoroacetate of the title compound) as white solid. The obtained white solid was desalinated under alkaline condition to give the title compound, which may be carried out, for example, by conventional process.

$^1$H NMR (400 MHz, methanol-d$_4$) δ 7.27 (d, J=8.0 Hz, 2H), 7.22 (d, J=8.0 Hz, 2H), 7.04 (s, 1H), 4.32 (t, J=6.6 Hz, 2H), 3.99 (s, 2H), 3.60 (s, 2H), 2.55-2.52 (m, 4H), 1.85-1.71 (m, 6H), 1.55-1.48 (m, 2H), 1.00 (t, J=7.4 Hz, 3H).

Preparation Example 2

The Compound of Formula II 2,4-dichloro-5-((2-(trimethylsilyl)ethoxy)methyl)-5H-pyrrolo[3,2-d]pyrimidine

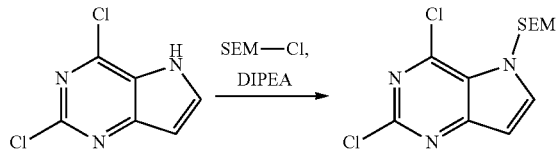 [SMILES: Clc1nc(Cl)c2[nH]ccc2n1 ; C[Si](C)(C)CCOCCl ; C[Si](C)(C)CCOCn1ccc2nc(Cl)nc(Cl)c21]

In DMF (20.00 L) was dissolved 2,4-dichloro-5H-pyrrolo[3,2-d]pyrimidine (4.00 kg, 21.28 mol), DIPEA (2.58 kg, 20.00 mol) was added in portions at room temperature (25° C.), and stirring was performed subsequently for 30 min. The reaction liquid was cooled to 0° C. with ice bath. Then SEM-Cl (4.00 kg, 24.00 mol) was added dropwise slowly at the speed of 1-2 drop/s over 5 h. After addition, the reaction was carried out at 0° C. for 4 h with stirring, and the reaction was monitored by HPLC until the reaction was completed. The reaction liquid was quenched and diluted with 70 L of water, and extracted with ethyl acetate (15 L×3). The combined organic phase was washed with 1 M hydrochloric acid aqueous solution (5 L×2) and saturated brine (7 L×2) successively. The solvent was removed by distillation under reduced pressure to give the title compound (6.40 kg, 20.11 mol, yield 94.50%).

$^1$H NMR (400 MHz, DMSO-d$_6$) δ 8.24-8.35 (m, 1H), 6.70-6.85 (m, 1H), 5.77 (s, 2H), 3.45-3.57 (m, 2H), 0.74-0.86 (m, 2H), 0.00 (s, 9H).

2-chloro-5-((2-(trimethylsilyl)ethoxy)methyl)-5H-pyrrolo[3,2-d]pyrimidin-4-amine

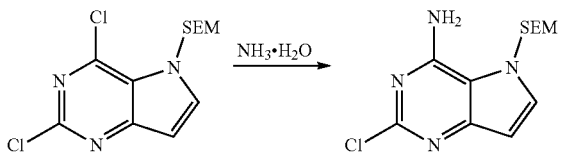 [SMILES: C[Si](C)(C)CCOCn1ccc2nc(Cl)nc(Cl)c21 ; "NH3·H2O" ; C[Si](C)(C)CCOCn1ccc2nc(Cl)nc(N)c21]

In isopropanol (1.60 L) was dissolved 2,4-dichloro-5-((2-(trimethylsily)ethoxy)methyl)-5H-pyrrolo[3,2-d]pyrimidine (1.60 kg, 5.03 mol) in 10 L autoclave. Aqueous ammonia (4 L) was added in one portion at room temperature (25° C.). The reaction mixture was stirred at 95° C. for 7 h and monitored by HPLC until the reaction was completed. The reaction liquid was allowed to cool to room temperature, and filtered through a Buchner funnel to give dark brown solid. The solid was slurried with ethyl acetate/n-heptane (1/1, 5 L×2) and ethyl acetate (4 L) successively to give the title compound as brown solid (1.25 kg, 4.18 mol, yield 83.1%).

$^1$H NMR (400 MHz, DMSO-d$_6$) δ 7.61-7.77 (m, 1H), 6.97-7.19 (m, 2H), 6.28-6.38 (m, 1H), 5.54-5.67 (m, 2H), 3.43-3.53 (m, 2H), 0.76-0.91 (m, 2H), 0.07 (s, 9H).

2-butoxy-5-((2-(trimethylsilyl)ethoxy)methyl)-5H-pyrrolo[3,2-d]pyrimidin-4-amine

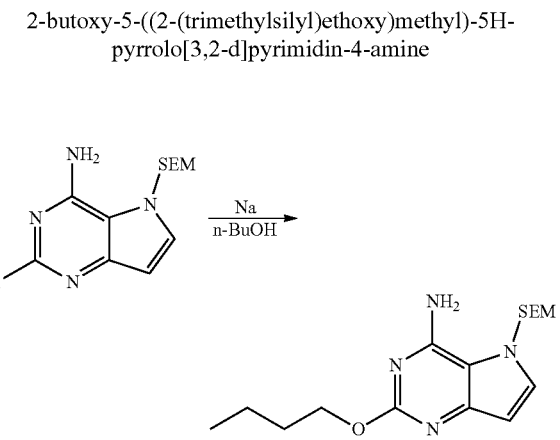

To n-BuOH (17.0 L) was slowly added sodium metal (525.05 g, 22.84 mol) in portions under nitrogen atmosphere. After addition, the system was heated to 60° C. and kept stirring at the temperature until sodium metal was dissolved completely. The system was cooled to 25° C., and 2-chloro-5-((2-(trimethylsilyl)ethoxy)methyl)-5H-pyrrolo[3,2-d]pyrimidin-4-amine (1.95 kg, 6.53 mol) was added in portions. After homogeneous mixing with stirring, the reactants were stirred at 90° C. for 8 h, and monitored by HPLC until the reaction was completed. The reaction liquid was allowed to cool to 25° C., poured into 30 L of saturated aqueous ammonium chloride solution slowly, and extracted with ethyl acetate (15 L×3). The combined organic phase was washed with saturated brine (20 L×2) and dried with anhydrous Na$_2$SO$_4$. After filtration, solvent was removed by distillation under reduced pressure and the residue was slurried in n-heptane (4 L).

Filtration was performed to give solid. The solid was then slurried with ethyl acetate (5 L) to give the title compound as yellow-white solid (1.53 kg, 4.55 mol, 69.7%).

$^1$H NMR (400 MHz, DMSO-d$_6$) δ 7.49-7.54 (m, 1H), 6.54-6.62 (m, 2H), 6.15-6.20 (m, 1H), 5.54 (s, 2H), 4.10-4.22 (m, 2H), 3.42-3.55 (m, 2H), 1.58-1.73 (m, 2H), 1.35-1.47 (m, 2H), 0.90-0.96 (m, 3H), 0.83-0.89 (m, 2H), 0.05 (s, 9H).

2-butoxy-5H-pyrrolo[3,2-d]pyrimidin-4-amine

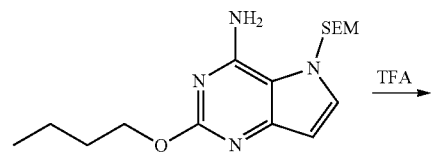

-continued

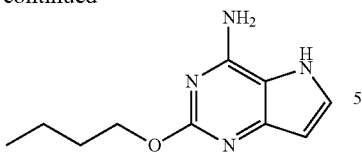

In TFA (5.50 L) was dissolved 2-butoxy-5-((2-(trimethylsilyl)ethoxy)methyl)-5H-pyrrolo[3,2-d]pyrimidin-4-amine (1.10 kg, 3.27 mol). The reaction liquid was stirred at 25° C. for 16 h, and monitored by HPLC until the reaction was completed. TFA was removed by distillation under reduced pressure. The residue was dissolved in methanol (1.2 L) and ice water (1.2 L), concentrated aqueous ammonia was used under uniform stirring to adjust pH to 12, and then stirring was performed for 2 h. Precipitate was precipitated out from solution continuously. The filter cake was white solid after filtration, which was slurried with 15% aqueous ammonia (1.2 L×3) and ethyl acetate (4 L) successively to give the title compound as white solid (550.00 g, 2.67 mol, 81.7%).

$^1$H NMR (400 MHz, methanol-$d_4$) δ 7.37 (d, J=2.89 Hz, 1H), 6.29 (d, J=3.01 Hz, 1H), 4.27 (t, J=6.53 Hz, 2H), 1.75 (d, J=7.91 Hz, 2H), 1.44-1.61 (m, 2H), 1.00 (t, J=7.40 Hz, 3H).

Examples of Pharmaceutical Activity

Toll-Like Receptor 7 and Toll-Like Receptor 8 In Vitro Receptor Binding Activity Screen Reagents:

HEK-blue hTLR7 cell and HEK-blue hTLR8 cell (available from InvivoGen)

DMEM medium heat inactivated fetal bovine serum

Anti Mycoplasma reagent Normocin™ bleomycin blasticidin

The structures of GS-9620 and R848 used are as follows, wherein the preparation of GS-9620 could be referred to the process disclosed in US20100143301; R848 was commercially available from ABGENT (IMG-2208, specification: 0.5 mg).

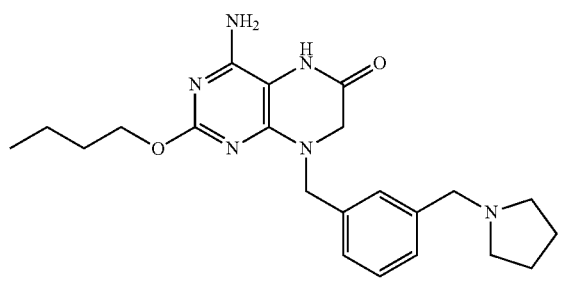

GS9620

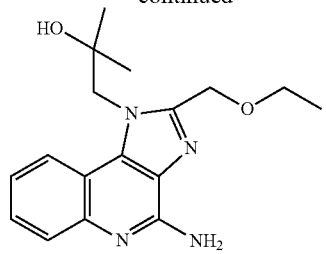

R848/Resiquimod

Scheme:

1. Preparation of 96-well compound plate:

The compounds were gradient diluted with DMSO in 3-fold using liquid work station POD starting at a concentration of 10 mmol/L and 10 points were diluted (2nd column to 11th column, and each point was duplicated). At 12th column, 1 μL of 5 mg/mL positive compound R848 was added as positive control; and at 1st column, 1 μL of DMSO was added as negative control. Each well contained 1 μL of DMSO.

2. The cells in culture flask were collected and the cell density was diluted to 250,000 cells/mL.

3. 200 μL (50,000 cells/well) of cell suspension was added into prepared compound plate and the final concentration of DMSO in each well was 0.5%.

4. The culture plates containing cells and the compounds were incubated in $CO_2$ incubator for 24 h at 37° C., 5% $CO_2$.

5. After 24 h incubation, 20 μL of supernatant was removed from each well to a 96-well transparent assay plate. To each well of the assay plate was added 180 μL of Quanti-Blue reagent and the plate was incubated in an incubator at 37° C., 5% $CO_2$ for 1 h.

6. After 1 h, the content of alkaline phosphatase in 20 μL of supernatant was determined using Microplate Reader OD650.

7. $EC_{50}$ of each compound was obtained with Prism software.

Results were shown in Table 1.

TABLE 1

| Compound | TLR7 $EC_{50}$ |
|---|---|
| Compound 1 | B |
| Compound 2 | C |
| Compound 3 | B |
| Compound 4 | B |
| Compound 5 | B |
| Compound 6 | C |
| Compound 7 | C |
| Compound 8 | B |
| Compound 9 | B |
| Compound 10 | B |
| Compound 11 | B |
| Compound 12 | B |
| Compound 13 | B |
| Compound 14 | B |
| Compound 15 | B |
| Compound 16 | B |

Note:
1 nM ≤ A ≤ 100 nM; 100 nM < B ≤ 1000 nM; 1000 nM < C ≤ 50 μM.

Results of compound 1 and control sample Toll-like receptor 7 agonist GS-9620 were shown in Table 2.

TABLE 2

| Samples (Title compound) | TLR7 EC$_{50}$ (nM) | TLR8 EC$_{50}$ (nM) |
| --- | --- | --- |
| GS-9620 | 517 | 7867 |
| Compound 1 | 160 | 11632 |

The compound according to the invention showed higher in vitro receptor binding activity to Toll-like receptor 7 than the control (Toll-like receptor 7 agonist GS-9620) and lower in vitro receptor binding activity to Toll-like receptor 8 than the control (Toll-like receptor 7 agonist GS-9620). The compound of the present invention has distinct selectivity differences with respect to different receptors, and the effect is superior over the prior art.

The invention claimed is:

1. A process for preparing the compound of formula I, comprising dehydroxylating the compound of formula VI to obtain the compound of formula I

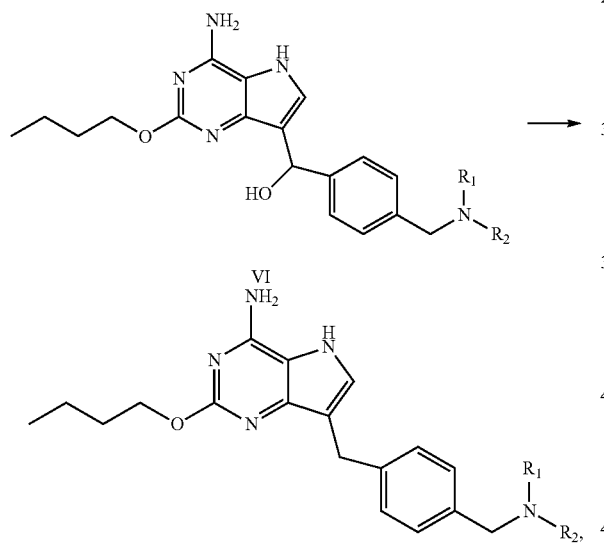

wherein
- R$_1$ and R$_2$ are independently selected from the group consisting of C$_{1-4}$ alkyl, or
- R$_1$ and R$_2$ together with the N atom attached thereto form 4-8 membered heterocycloalkyl, wherein the heterocycloalkyl is optionally substituted with one or more substituents independently selected from the group consisting of hydroxyl, halogen, C$_{1-4}$ alkyl and C$_{1-4}$ alkoxy; and
- wherein the dehydroxylating is performed in the presence of triethylsilane and trifluoroacetic acid.

2. The process according to claim 1, comprising the following steps:

(a) reacting the compound of formula II with the compound of formula III in the presence of base to obtain the compound of formula IV

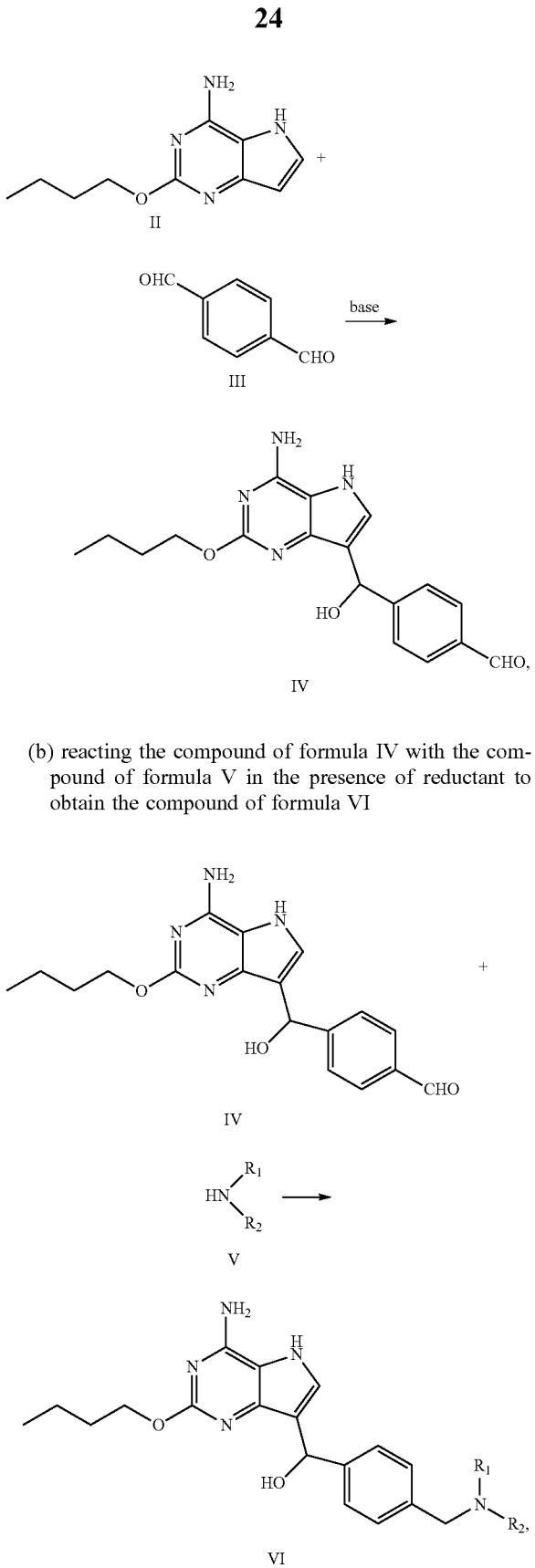

(b) reacting the compound of formula IV with the compound of formula V in the presence of reductant to obtain the compound of formula VI (c) dehydroxylating the compound of formula VI to obtain the compound of formula I

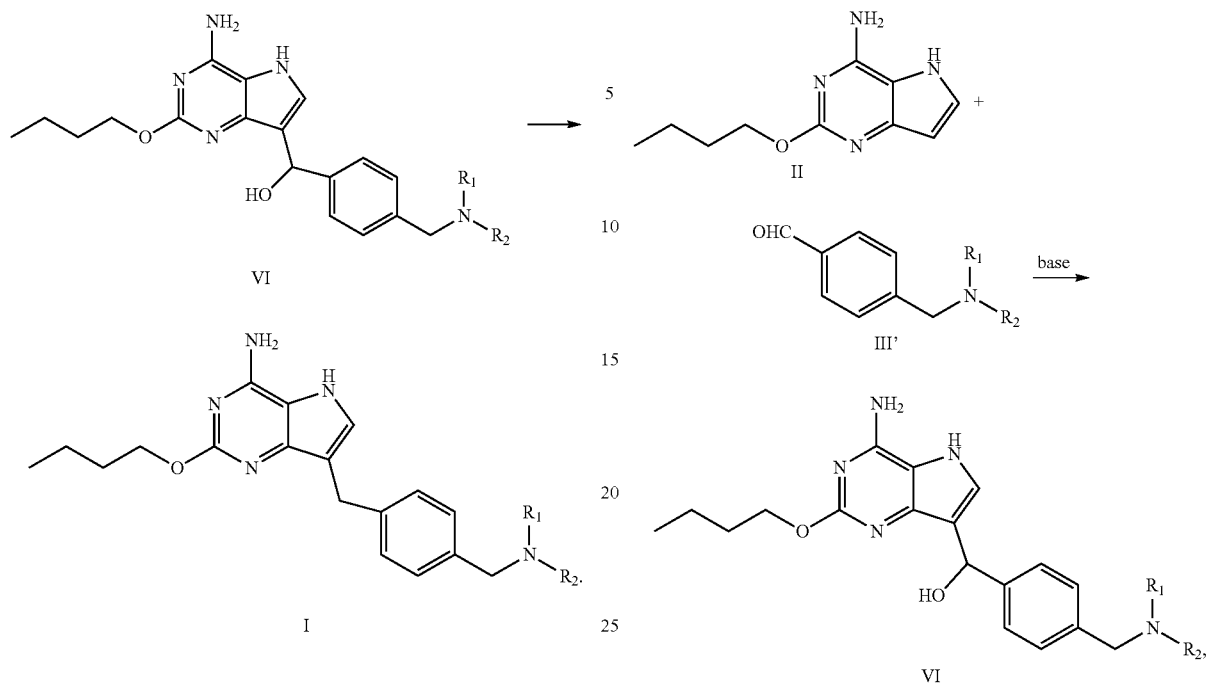

wherein the dehydroxylating is performed in the presence of triethylsilane and trifluoroacetic acid.

3. The process according to claim 2, wherein the compound of formula V is selected from:

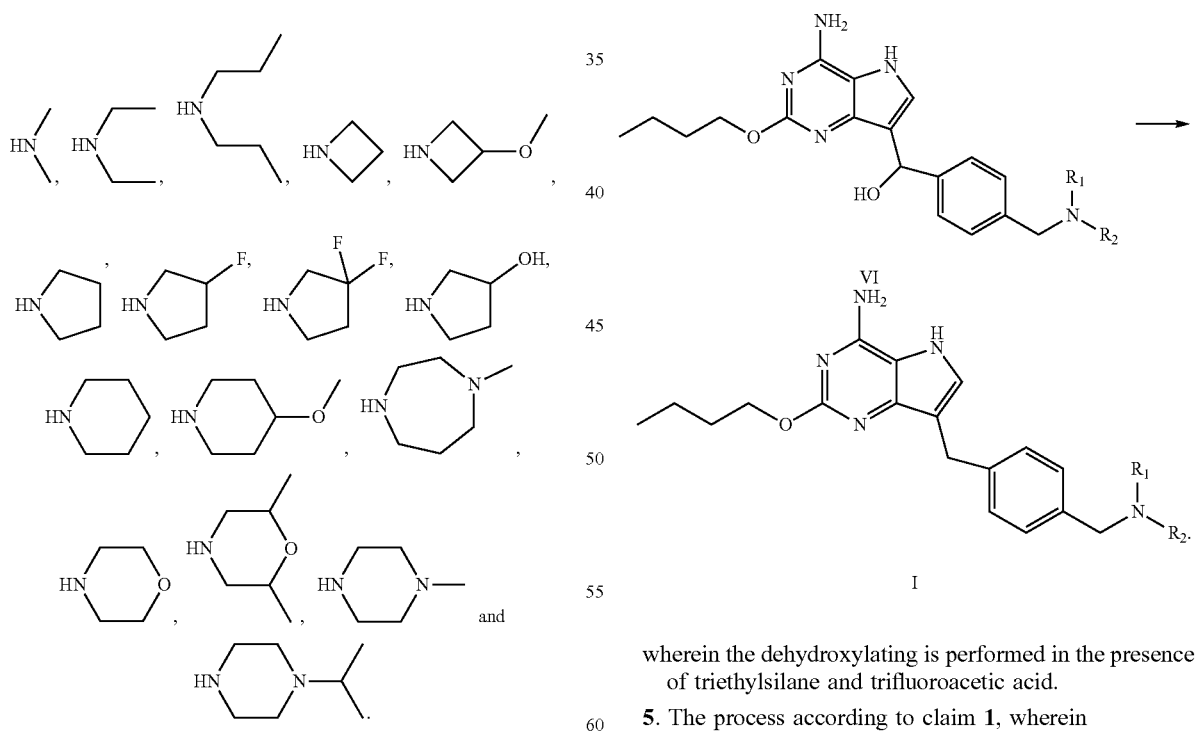

4. The process according to claim 1, wherein the process comprises the following steps:
(a') reacting the compound of formula II with the compound of formula III' in the presence of base to obtain the compound of formula VI (b') dehydroxylating the compound of formula VI to obtain the compound of formula I wherein the dehydroxylating is performed in the presence of triethylsilane and trifluoroacetic acid.

5. The process according to claim 1, wherein
the molar ratio of the compound of formula VI to the triethylsilane is 1:1-1:10;
the molar ratio of the compound of formula VI to the trifluoroacetic acid is 1:2-1:20.

6. The process according to claim 1, wherein the compound of formula I is selected from:

1
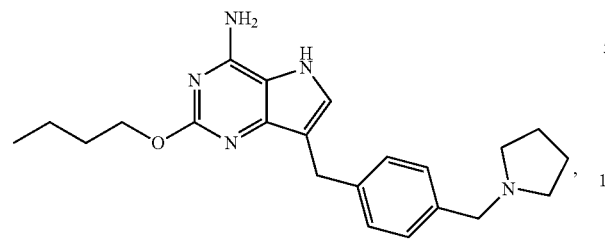
2
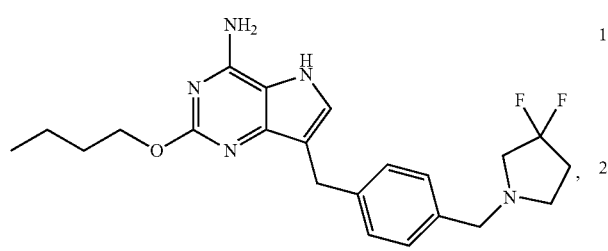
3
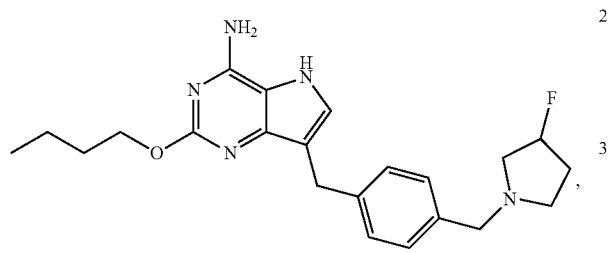
4
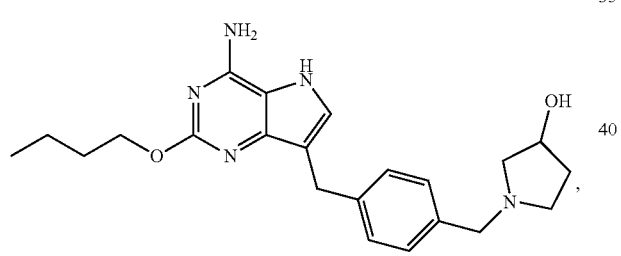
5
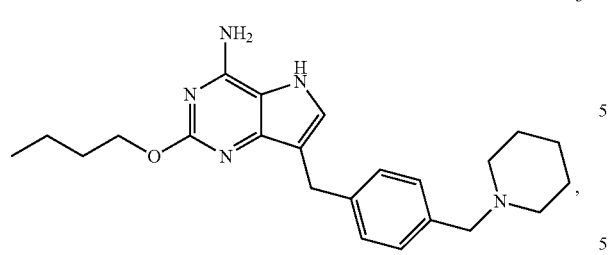
6
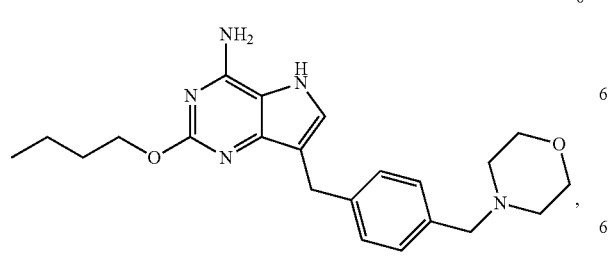
7
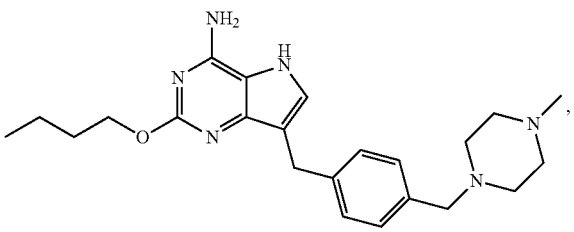
8
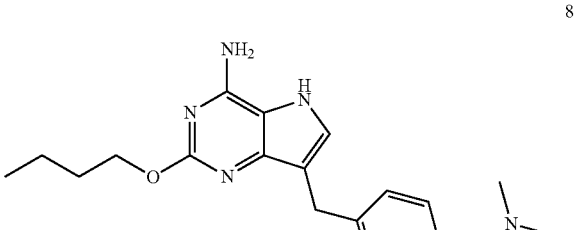
9
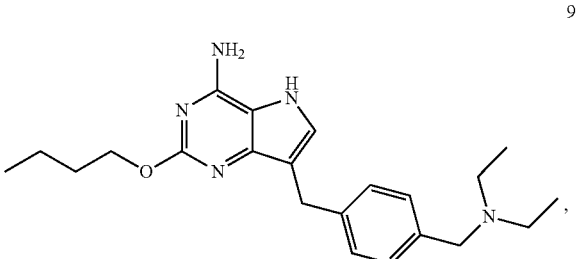
10
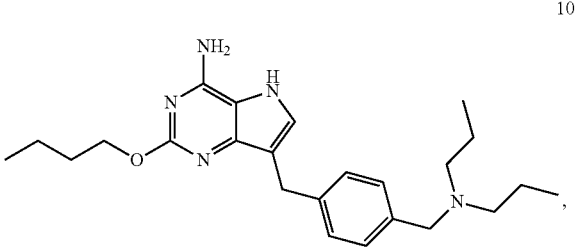
11
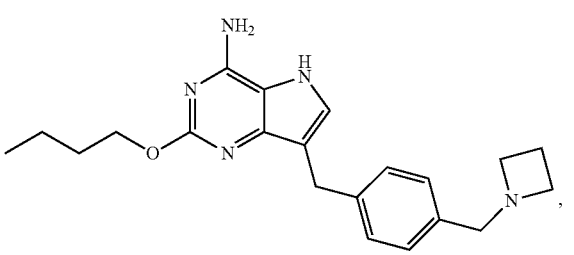
12
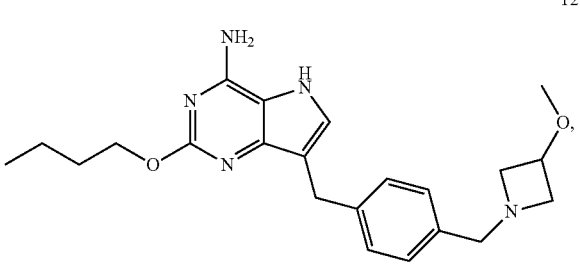

-continued

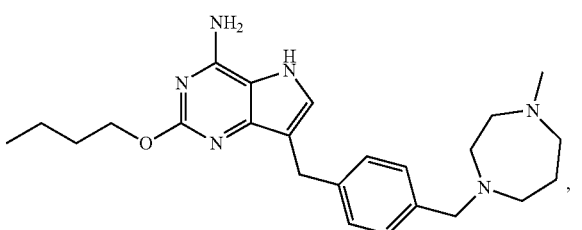

13

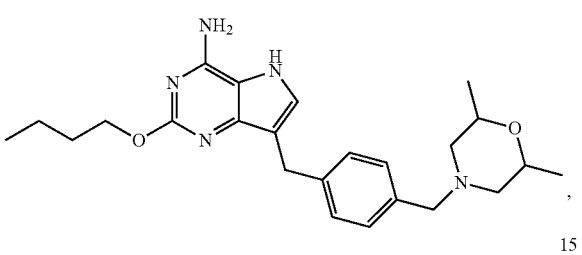

14

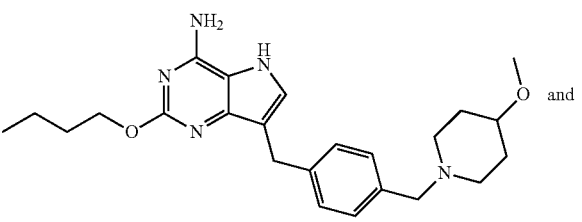

15

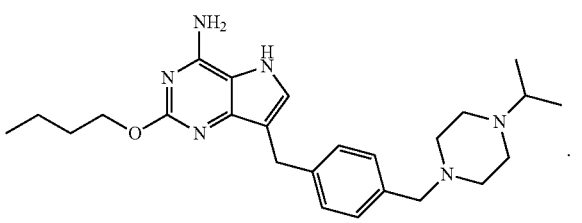 and

16

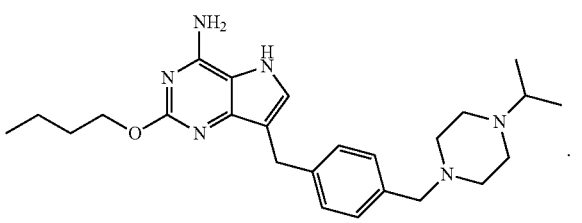

7. The process according to claim 3, wherein the compound of formula V is

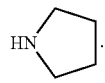

8. The process according to claim 5, wherein the molar ratio of the compound of formula VI to the triethylsilane is 1:2-1:8.

9. The process according to claim 5, wherein the molar ratio of the compound of formula VI to the triethylsilane is 1:5.

10. The process according to claim 5, wherein the molar ratio of the compound of formula VI to the trifluoroacetic acid is 1:5-1:15.

11. The process according to claim 5, wherein the molar ratio of the compound of formula VI to the trifluoroacetic acid is 1:10-1:12.

12. The process according to claim 2, wherein the base in step (a) is selected from the group consisting of sodium carbonate, sodium bicarbonate, potassium carbonate, potassium phosphate, potassium bicarbonate, cesium carbonate, lithium hydroxide, sodium hydroxide, potassium hydroxide, calcium hydroxide, magnesium hydroxide, barium hydroxide, sodium methoxide, sodium ethoxide, sodium t-butoxide, potassium t-butoxide, triethylamine, diisopropylethylamine, pyridine, N,N-dimethylaminopyridine, piperidine, N-methylpiperidine, morpholine, N-methylmorpholine, and any combination thereof.

13. The process according to claim 2, wherein step (b) is performed in the presence of acid.

14. The process according to claim 13, wherein the acid is selected from the group consisting of hydrochloric acid, hydrobromic acid, phosphoric acid, sulfuric acid, formic acid, acetic acid, propionic acid, citric acid, fumaric acid, malic acid, succinic acid, salicylic acid, maleic acid, trifluoroacetic acid, and any combination thereof.

15. The process according to claim 2, wherein the reductant in step (b) is selected from the group consisting of $BH_3$, $NaBH_4$, $NaBH_3CN$, $NaBH(AcO)_3$, and any combination thereof.

16. The process according to claim 15, wherein the reductant is $NaBH(AcO)_3$.

17. The process according to claim 4, wherein the base in step (a') is selected from the group consisting of sodium carbonate, sodium bicarbonate, potassium carbonate, potassium phosphate, potassium bicarbonate, cesium carbonate, lithium hydroxide, sodium hydroxide, potassium hydroxide, calcium hydroxide, magnesium hydroxide, barium hydroxide, sodium methoxide, sodium ethoxide, sodium t-butoxide, potassium t-butoxide, triethylamine, diisopropylethylamine, pyridine, N,N-dimethylaminopyridine, piperidine, N-methylpiperidine, morpholine, N-methylmorpholine, and any combination thereof.

* * * * *